United States Patent
Bhamre

(10) Patent No.: US 8,357,128 B2
(45) Date of Patent: Jan. 22, 2013

(54) PORTABLE EYE-WIPING DEVICE

(76) Inventor: Shrikant S Bhamre, New York, NY (US)

( * ) Notice: Subject to any disclaimer, the term of this patent is extended or adjusted under 35 U.S.C. 154(b) by 584 days.

(21) Appl. No.: 12/581,932

(22) Filed: Oct. 20, 2009

(65) Prior Publication Data
US 2011/0092923 A1    Apr. 21, 2011

(51) Int. Cl.
*A61F 7/02* (2006.01)
*H05B 3/06* (2006.01)
(52) U.S. Cl. .............. 604/291; 219/386; 219/524
(58) Field of Classification Search ............ 604/291
See application file for complete search history.

(56) References Cited

U.S. PATENT DOCUMENTS

| | | | | |
|---|---|---|---|---|
| 1,563,985 A * | 12/1925 | Hoddersen-Balling | ......... | 99/351 |
| 2,181,821 A | 11/1939 | Seals | | |
| 2,198,989 A * | 4/1940 | Cooley | ........... | 604/291 |
| 2,889,443 A | 6/1959 | Dobmeier | | |
| 2,920,243 A * | 1/1960 | Taren | .............. | 219/270 |
| 2,924,167 A * | 2/1960 | Rhodes | ........... | 99/337 |
| 3,060,918 A * | 10/1962 | Meyer | ............ | 126/9 R |
| 3,167,805 A | 2/1965 | Zuppinger et al. | | |
| 3,186,540 A * | 6/1965 | Breger | .............. | 206/5 |
| 3,410,985 A * | 11/1968 | Giacchero | ........ | 219/222 |
| 3,983,362 A * | 9/1976 | Hoogesteger et al. | ........ | 219/521 |
| 4,044,226 A * | 8/1977 | Kadlecik et al. | .............. | 219/521 |
| 4,167,942 A * | 9/1979 | Brunelli | ......... | 604/298 |
| 4,279,933 A * | 7/1981 | Austin et al. | .............. | 426/124 |
| 4,332,319 A * | 6/1982 | Hurwood | ........ | 206/210 |
| 4,427,111 A * | 1/1984 | Laipply | ............ | 206/210 |
| 4,510,641 A | 4/1985 | Morris | | |
| 4,553,665 A * | 11/1985 | Weick et al. | ........ | 206/37 |
| 4,622,161 A | 11/1986 | Cornelissens et al. | | |
| 4,638,521 A * | 1/1987 | Potente et al. | ........ | 15/117 |
| 4,696,393 A * | 9/1987 | Laipply | ............ | 206/210 |
| 4,783,541 A | 11/1988 | Eichler et al. | | |
| 4,810,859 A * | 3/1989 | Anabtawi et al. | ............ | 219/535 |
| 4,828,113 A | 5/1989 | Friedland et al. | | |
| 4,836,368 A * | 6/1989 | Cotton | ............ | 206/205 |
| 4,857,708 A * | 8/1989 | DeMars | ........ | 219/385 |
| 4,880,951 A * | 11/1989 | Levinson | ........ | 219/733 |
| D309,844 S | 8/1990 | Storsberg | | |
| 4,973,827 A * | 11/1990 | Nozaki | ........... | 219/521 |
| 5,210,396 A * | 5/1993 | Sanders | ........ | 219/521 |
| 5,328,053 A * | 7/1994 | Cook et al. | .......... | 221/63 |
| 5,738,082 A * | 4/1998 | Page et al. | .......... | 126/263.01 |
| 5,809,573 A * | 9/1998 | Bary | ........... | 2/209 |
| 5,839,842 A | 11/1998 | Wanat et al. | | |
| 6,150,635 A * | 11/2000 | Hannon et al. | ........ | 219/386 |
| 6,170,664 B1 * | 1/2001 | Dar | ........ | 206/5.1 |
| 6,202,845 B1 * | 3/2001 | Hill | ........ | 206/449 |
| 6,286,666 B1 * | 9/2001 | Umdasch | .......... | 206/5.1 |
| 6,316,750 B1 * | 11/2001 | Levin | ............. | 219/438 |
| 6,331,696 B1 * | 12/2001 | Nakamura et al. | ........... | 219/386 |

(Continued)

FOREIGN PATENT DOCUMENTS
EP    0860131 A1 *   8/1998

*Primary Examiner* — Melanie Hand
*Assistant Examiner* — Paula Craig
(74) *Attorney, Agent, or Firm* — Michael J. Feigin, Esq.; Feigin & Associates, LLC

(57) ABSTRACT

A portable heater with ovoid receptacle is disclosed. The portable heater comprises a top member comprising a semi-ovoid cavity, a bottom member comprising a semi-ovoid cavity, a hinge operatively connected to the top and bottom members, and a heating mechanism.

12 Claims, 11 Drawing Sheets

U.S. PATENT DOCUMENTS

| | | | |
|---|---|---|---|
| 6,392,196 B1 * | 5/2002 | Lin | 219/211 |
| 6,525,299 B2 * | 2/2003 | Hannon et al. | 219/436 |
| 6,528,766 B1 * | 3/2003 | Parks et al. | 219/386 |
| 6,758,132 B1 * | 7/2004 | Kuo et al. | 99/340 |
| 6,902,338 B2 | 6/2005 | Puvvada et al. | |
| 6,903,307 B1 * | 6/2005 | McConnell et al. | 219/401 |
| 6,935,133 B2 | 8/2005 | Keeter et al. | |
| 7,022,945 B1 * | 4/2006 | Western | 219/386 |
| 7,053,337 B2 * | 5/2006 | Ragan et al. | 219/386 |
| 7,094,992 B1 * | 8/2006 | Wray et al. | 219/386 |
| 7,441,660 B2 | 10/2008 | Caron | |
| 7,540,376 B2 * | 6/2009 | Mahieu et al. | 206/5.1 |
| 7,638,740 B1 * | 12/2009 | Hradecky | 219/524 |
| 7,699,166 B2 * | 4/2010 | Gauger et al. | 206/233 |
| 7,976,573 B2 * | 7/2011 | Korb et al. | 607/96 |
| 2003/0155343 A1 * | 8/2003 | Ibanez | 219/386 |
| 2004/0065658 A1 * | 4/2004 | Damiano et al. | 219/524 |
| 2004/0226454 A1 * | 11/2004 | Pirkle et al. | 99/331 |
| 2004/0262287 A1 * | 12/2004 | Ragan et al. | 219/438 |
| 2005/0119629 A1 * | 6/2005 | Soroudi | 604/289 |
| 2005/0126556 A1 * | 6/2005 | Bossler | 126/25 R |
| 2005/0133382 A1 * | 6/2005 | Gerard et al. | 206/5.1 |
| 2005/0148260 A1 * | 7/2005 | Kopacz et al. | 442/381 |
| 2006/0191901 A1 * | 8/2006 | Taylor et al. | 219/521 |
| 2006/0196492 A1 * | 9/2006 | Whitmer | 126/25 R |
| 2006/0210616 A1 * | 9/2006 | Linder | 424/449 |
| 2006/0276356 A1 * | 12/2006 | Panandiker et al. | 510/100 |
| 2007/0000144 A1 * | 1/2007 | Beson | 34/201 |
| 2007/0148198 A1 * | 6/2007 | Joseph et al. | 424/401 |
| 2007/0278242 A1 * | 12/2007 | Amundson et al. | 221/63 |
| 2007/0289988 A1 * | 12/2007 | Sosalla et al. | 221/150 A |
| 2008/0053860 A1 * | 3/2008 | McDonald | 206/494 |
| 2009/0062172 A1 * | 3/2009 | Cunningham et al. | 510/281 |
| 2009/0118684 A1 * | 5/2009 | Da Silva et al. | 604/290 |
| 2009/0308373 A1 * | 12/2009 | Scott et al. | 126/25 R |
| 2010/0095946 A1 * | 4/2010 | Creel | 126/25 R |
| 2010/0125255 A1 * | 5/2010 | Paulson | 604/291 |
| 2010/0258106 A1 * | 10/2010 | Simms, II | 126/25 R |
| 2011/0015463 A1 * | 1/2011 | Legendre et al. | 600/9 |
| 2012/0193344 A1 * | 8/2012 | Chen | 219/385 |

* cited by examiner

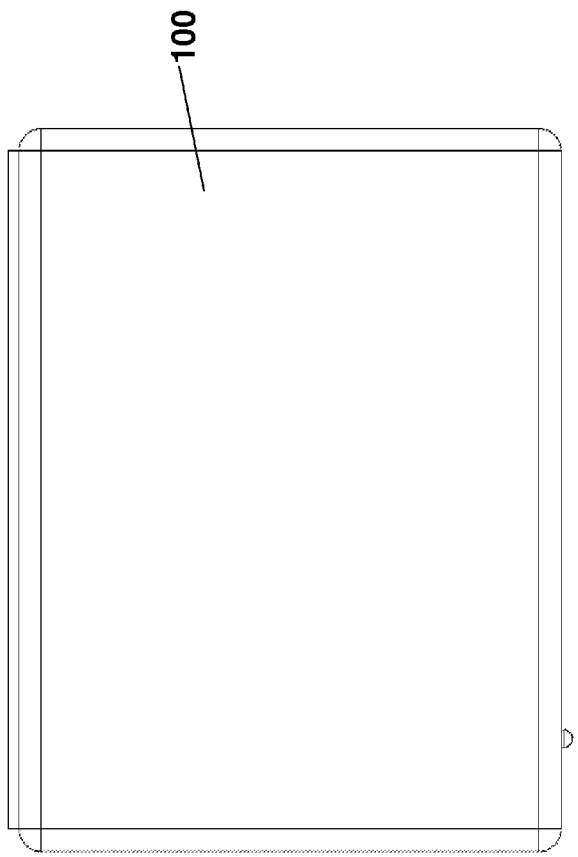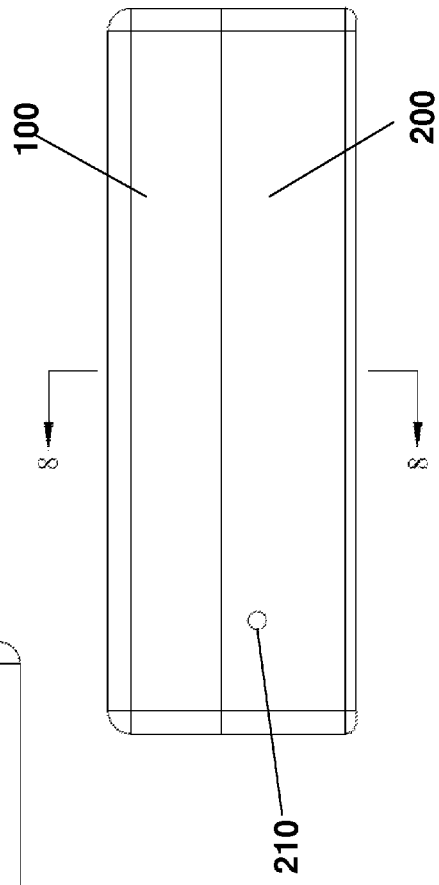
Figure 3
Figure 4

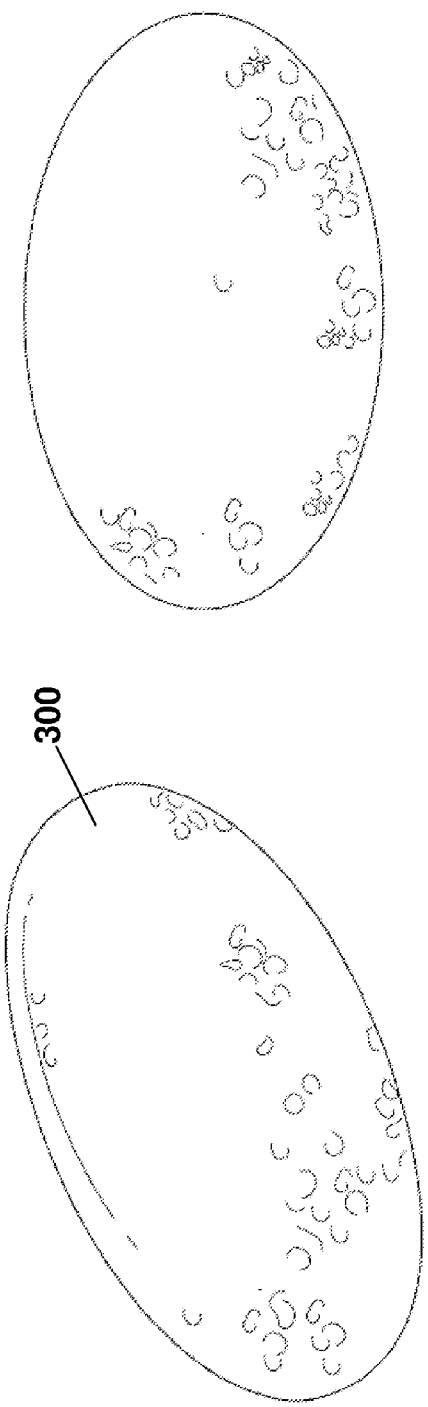
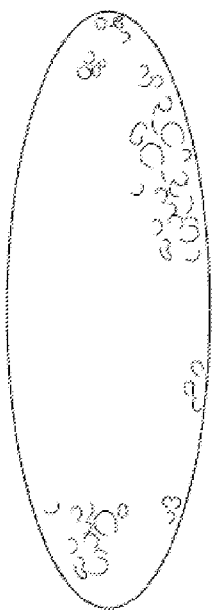
Figure 9
Figure 10
Figure 11

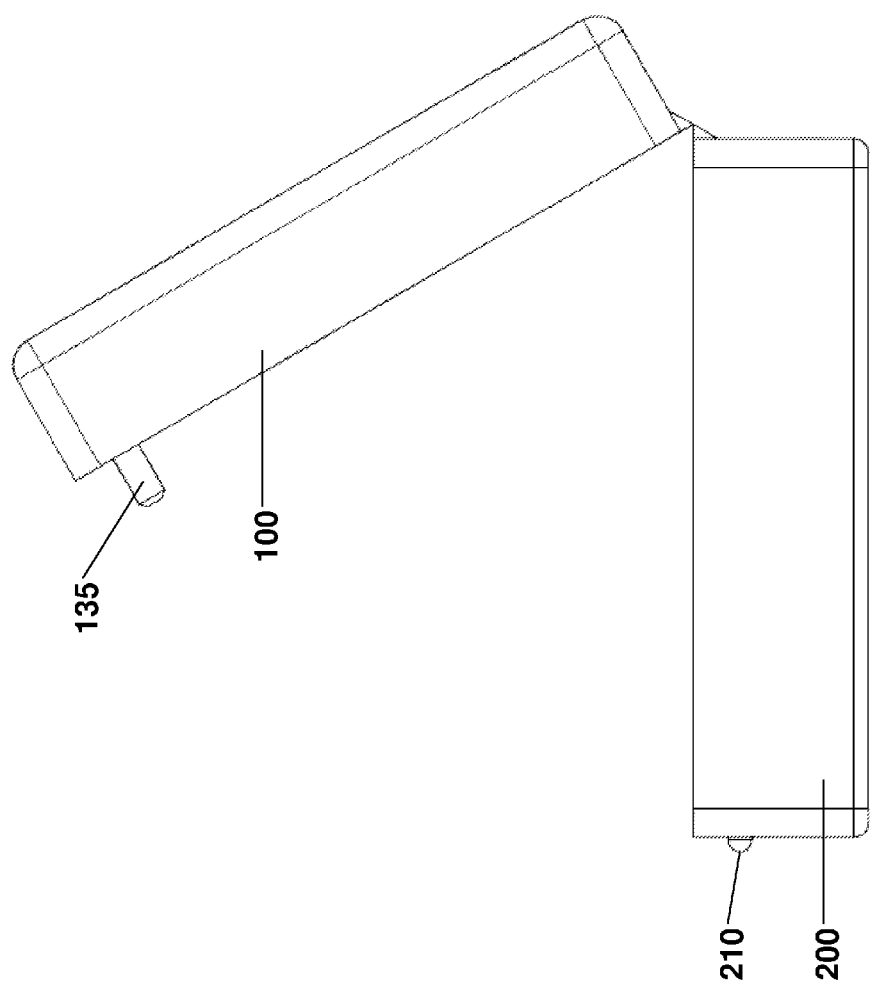

PORTABLE EYE-WIPING DEVICE

FIELD OF THE DISCLOSED TECHNOLOGY

The disclosed technology relates generally to hinged heating devices and, more specifically, to portable heating devices with receptacles.

BACKGROUND OF THE DISCLOSED TECHNOLOGY

The meibomian gland in the eyelid secretes sebum, an oily/waxy substance used to lubricate the eye and produce tears. To date, more than ninety different proteins have been identified in sebum, but what is relevant to the average person is a certain stickiness or crustiness that develops around the eye, especially overnight when the sebum often collects and dries at the edge of the eye. Dysfunctional meibomian glands may cause dry eyes, blepharitis (infected skin resulting from the dry eyeball rubbing off small pieces of skin from the eyelid), meibomitis (inflammation of the meibomian gland), meibomian gland dysfunction, and similar complications resulting from the secretions. Many vague symptoms, such as dryness, contact lens-induced irritation, burning, and the like may persist for months or years. The general hygiene of the individual may play a large role in such problems as well, and when the required prophylactic procedures are onerous, time consuming, or easy to forget (such as tooth-flossing, cleaning behind one's ears, or removing eye sebum) a person may simply neglect the activity more often than advisable.

In the current state of the art, the accepted treatment to remove excess sebum secretions is to use a mild detergent, such as baby shampoo, and wiping the closed eyelid several times. Alternatively, warm water—plain or diluted with such a detergent—may be applied to aid in dissolving the solidified sebum. Other known methods are the use of eye drops, though such products typically have an undesired degree of toxicity. While vials containing eye drops are easily portable, many ophthalmologists hesitate to prescribe such medication due to toxicology concerns, and it is neither easy nor comfortable to warm up eye drops before application. Baby shampoo and cloth or wipes, on the other hand, are not as portable and require greater effort on the part of the user, including preparation, use of towels or tissues, and cleanup.

What is needed is a device or method to allow eye hygiene to be accomplished in a safe, comfortable, effective, and simple manner. Such a device or method would enable a higher degree of hygiene and comfort for the user compared to what is currently known in the art.

SUMMARY OF THE DISCLOSED TECHNOLOGY

It is therefore an object of the disclosed technology to provide a portable, easy to use heating device and wipes which may be used for any cleaning purpose, but also, specifically designed to clean sebum from the face of a person, and more specifically, the region around the eye.

In one aspect of the disclosed technology, a portable heater with an ovoid-shaped receptacle is claimed. Ovoid, in embodiments of the disclosed technology refers to a solid generated from an oval curve in a plane, rotated around one of its axes of symmetry, an elongated sphere, or a three dimensional space resembling such a shape. The portable heater comprises a top member comprising a semi-ovoidal cavity, a bottom member comprising a semi-ovoidal cavity, a hinge operatively connected to the top and bottom members, and a heating mechanism.

The semi-ovoid cavities of the top and bottom members may form a unitary ovoid cavity in a closed configuration of the portable heater. The top member may comprise at least one pin and the bottom member may comprise at least one recess. The heating mechanism may be placed in an active mode only when the pin(s) and recess(es) interface. The two semi-ovoid cavities may be substantially identical (e.g., be half-ovoid or appear as such to a casual observer, and/or identical with respect to the tolerance level of the machinery used to produce the cavities).

A detergent-soaked pad may be adapted for placement in the unitary ovoid cavity. To aid in even heat distribution/retention of detergent within the pad during heating, the pad may be foil-lined. To promote usability, the exterior of the pad may be porous and/or textured.

A method for removing sebum from a face comprises warming a textured pad in an ovoid-shaped cavity of a portable heater, removing the pad from the heater, and gently wiping the pad across at least a portion of the face. The textured pad may be ovoid-shaped and may further be pre-soaked in oil.

In a further embodiment of the disclosed technology, a case comprises a battery compartment, a first and second semi-ovoid cavity, and at least one metal heating mechanism situated within the case operatively connected to the battery compartment and the semi-ovoid cavity. A second metal heating mechanism situated within the case and operatively connected to a battery compartment and a second semi-ovoid cavity may further be present A first member may comprise the first semi-ovoid cavity and a second member may comprise a second semi-ovoid cavity, and the members may be attached by hinges. Unless at least one pin of the first member and at least one corresponding recess of the second member are engaged, said heating mechanism may be non-operative.

A kit comprising a portable heater with ovoid receptacle and ovoid pad, the pad being pre-moisturized with a cleaning agent, is further claimed. The cleaning agent may be any one of an oil, detergent, sterile water, and/or combination thereof. The ovoid pad may be wrapped in foil. A first member may comprise a first half of the ovoid receptacle, and a second member may comprise a second half of the ovoid receptacle. The first and second members may be attached by hinges.

BRIEF DESCRIPTION OF THE DRAWINGS

FIG. 3 shows a bottom plan view of an eye-wiping device in an embodiment of the disclosed technology.

FIG. 4 shows a front elevation view of an eye-wiping device in a closed configuration in an embodiment of the disclosed technology.

FIG. 9 shows a top perspective view of a pad adapted for placement in an ovoid cavity in an embodiment of the disclosed technology.

FIG. 10 shows a top plan view of a pad adapted for placement in an ovoid cavity in an embodiment of the disclosed technology.

FIG. 11 shows a side view of a pad adapted for placement in an ovoid cavity in an embodiment of the disclosed technology.

FIG. 17 shows a side view of an eye-wiping device in an open configuration in an embodiment of the disclosed technology.

DETAILED DESCRIPTION OF EMBODIMENTS OF THE DISCLOSED TECHNOLOGY

Embodiments of the disclosed technology comprise a case with an ovoid-shaped receptacle therein, and a mechanism, such as battery power, to warm an object, such as a pad adapted for placement therein, placed in the ovoid receptacle. In an embodiment thereof, the device comprises a top and bottom member, each comprising a semi-ovoid cavity, such as a half-ovoid cavity, each semi-ovoid cavity formed from, or adjacent to, a heating mechanism, such as a concave metal plate heated with the aid of a battery or other power source. Safety mechanisms ensuring that the device is non-operational when in an open configuration and/or that unsafe temperatures of a pad are not reached are also contemplated and disclosed herein. The ovoid cavity and a corresponding pad allow for such a pad having oil, chemicals, or the like to be warmed and optimally used to wipe away sebum or other non-wanted substances, food, or other particles from a surface such as the skin.

Embodiments of the disclosed technology will become clearer when reviewed in connection with the description of the figures herein below.

Figure 1:
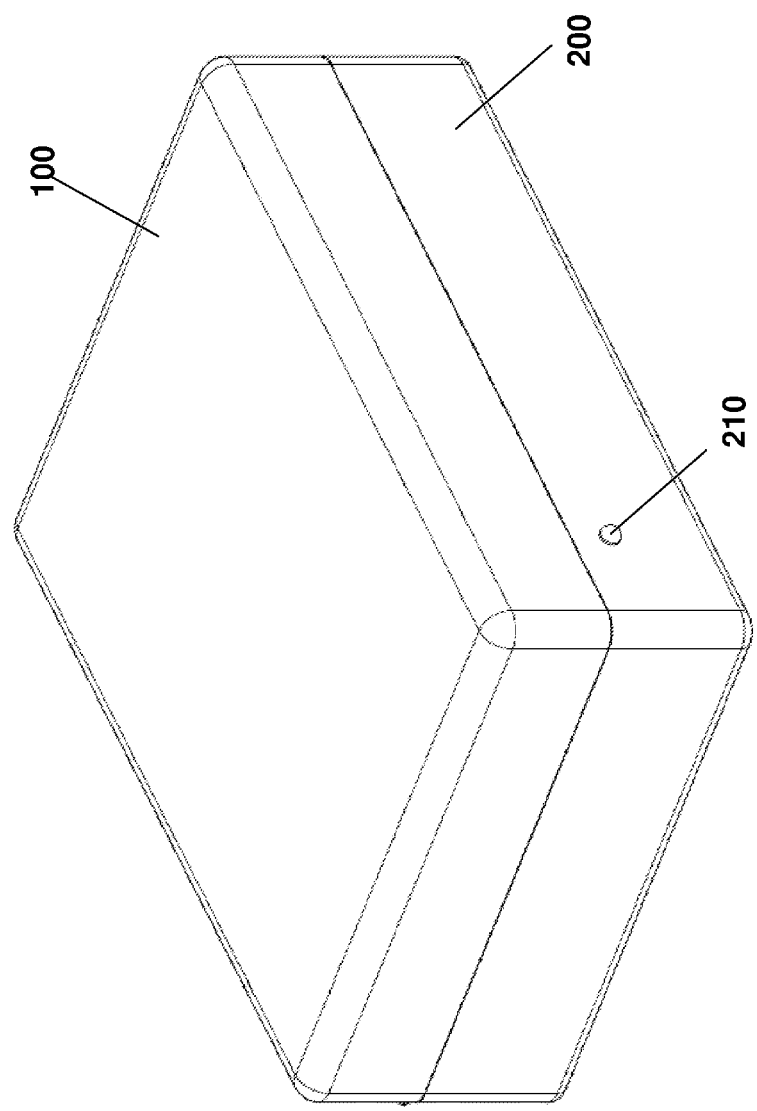
FIG. 1 shows a top, front perspective view of an eye-wiping device in a closed configuration in an embodiment of the disclosed technology.

FIG. 1 shows a top, front perspective view of an eye-wiping device in a closed configuration in an embodiment of the disclosed technology. A top member 100 and bottom member 200 are used to house an ovoid or other shaped cavity which, in embodiments of the disclosed technology, correspond to/are able to receive a correspondingly-shaped pad. The pad is warmed therein, as the warmth is more comfortable than room-temperature or below room-temperature liquids or solids on the face and allows a user to more effectively wipe away sebum or other unwanted particles. Still further, most liquids, such as those described below with respect to FIGS. 9 through 11, are more effective/more easily absorbed at higher temperatures. When a desired pre-defined temperature is reached, as measured by a timer or thermometer within, or associated with, the ovoid cavity, an indicator light 210 comes on in embodiments of the disclosed technology. The indicator 210, in an embodiment of the disclosed technology, lights a first color, such as red, to indicate heating is taking place, and a second color, such as green, to indicate that the desired temperature has been reached or that it is safe to open the device and take out the pad placed therein.

Figure 2:
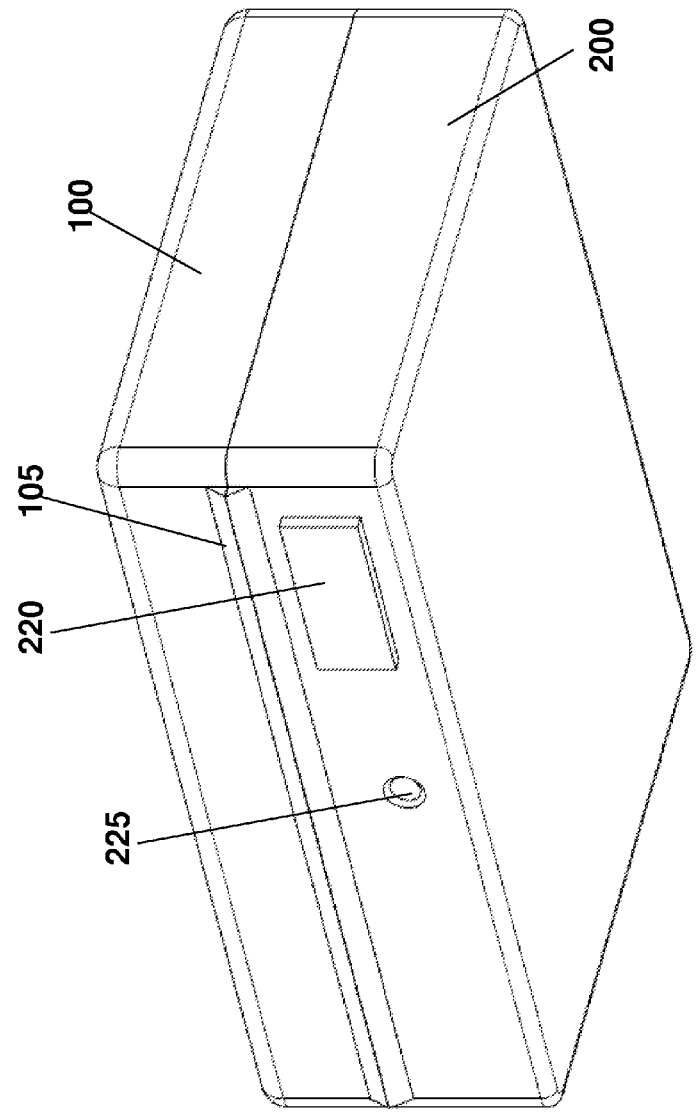
FIG. 2 shows a bottom, rear perspective view of an eye-wiping device in a closed configuration in an embodiment of the disclosed technology.

FIG. 2 shows a bottom, rear perspective view of an eye-wiping device in a closed configuration in an embodiment of the disclosed technology. A hinge 105, in this embodiment, connects the top member 100 to the bottom member 200, such that a user may open and close the device in order to access the ovoid receptacle and place or remove a pad, such as an ovoid pad. Battery compartment 220 allows a user to place one or more batteries into the device, so that the device can be used anywhere, such as on an airplane, in a car, while sitting in a park, at a restaurant, at a hotel, or the like. Further, a electrical port 225 or wireless charging mechanism is provided in embodiments of the disclosed technology making it possible to power the device via an electrical connection to a power source, such as a common electrical outlet, or to recharge a rechargeable battery placed within battery compartment 220.

Figure 5:
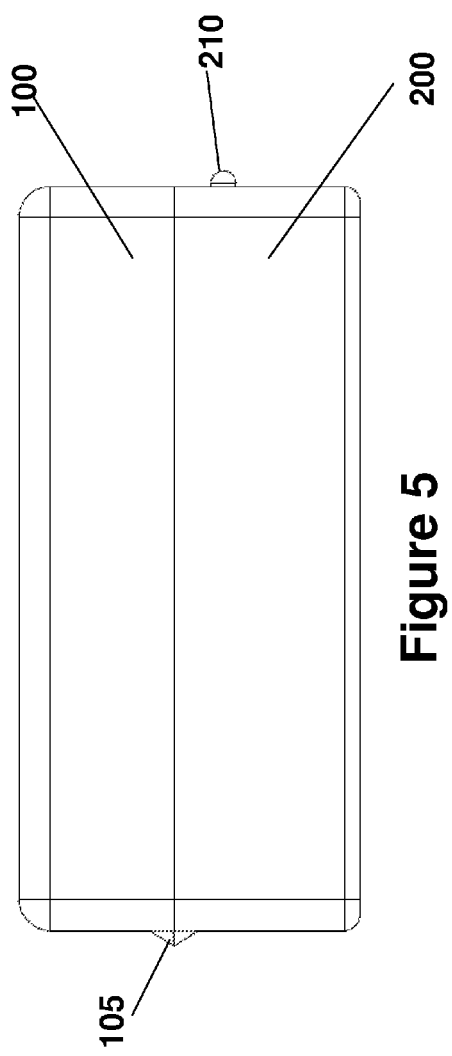
FIG. 5 shows a side elevation view of an eye-wiping device in a closed configuration in an embodiment of the disclosed technology.
Figure 6:
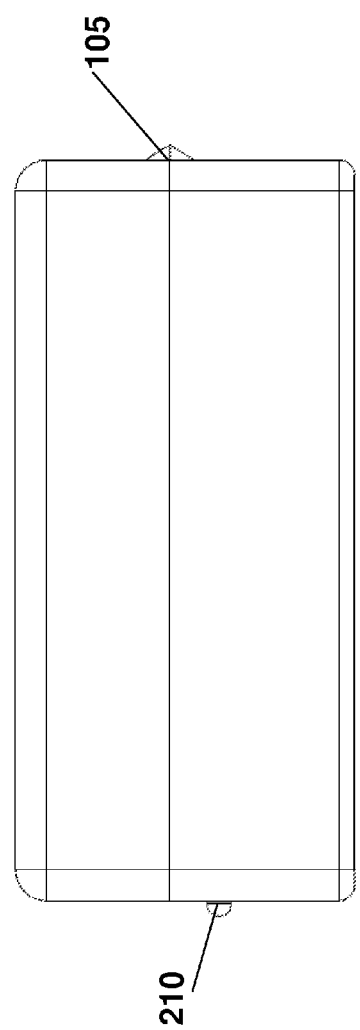
FIG. 6 shows an opposite side elevation view of an eye-wiping device in a closed configuration in an embodiment of the disclosed technology.

FIG. 3 shows a bottom plan view of an eye-wiping device in an embodiment of the disclosed technology. FIG. 4 shows a front elevation view of an eye-wiping device in a closed configuration in an embodiment of the disclosed technology. FIG. 5 shows a side elevation view of an eye-wiping device in a closed configuration in an embodiment of the disclosed technology. FIG. 6 shows an opposite side elevation view of an eye-wiping device in a closed configuration in an embodiment of the disclosed technology. These various views show the full dimensions of such a device in an embodiment of the disclosed technology. The dimensions, in this embodiment, are 4 inches×3 inches, with a height of approximately ¾ inch. Such dimensions include space for the interior components of the device, a compartment for unused wipes (not shown) and for the device to fit within pockets of a variety of sizes.

Figure 7:
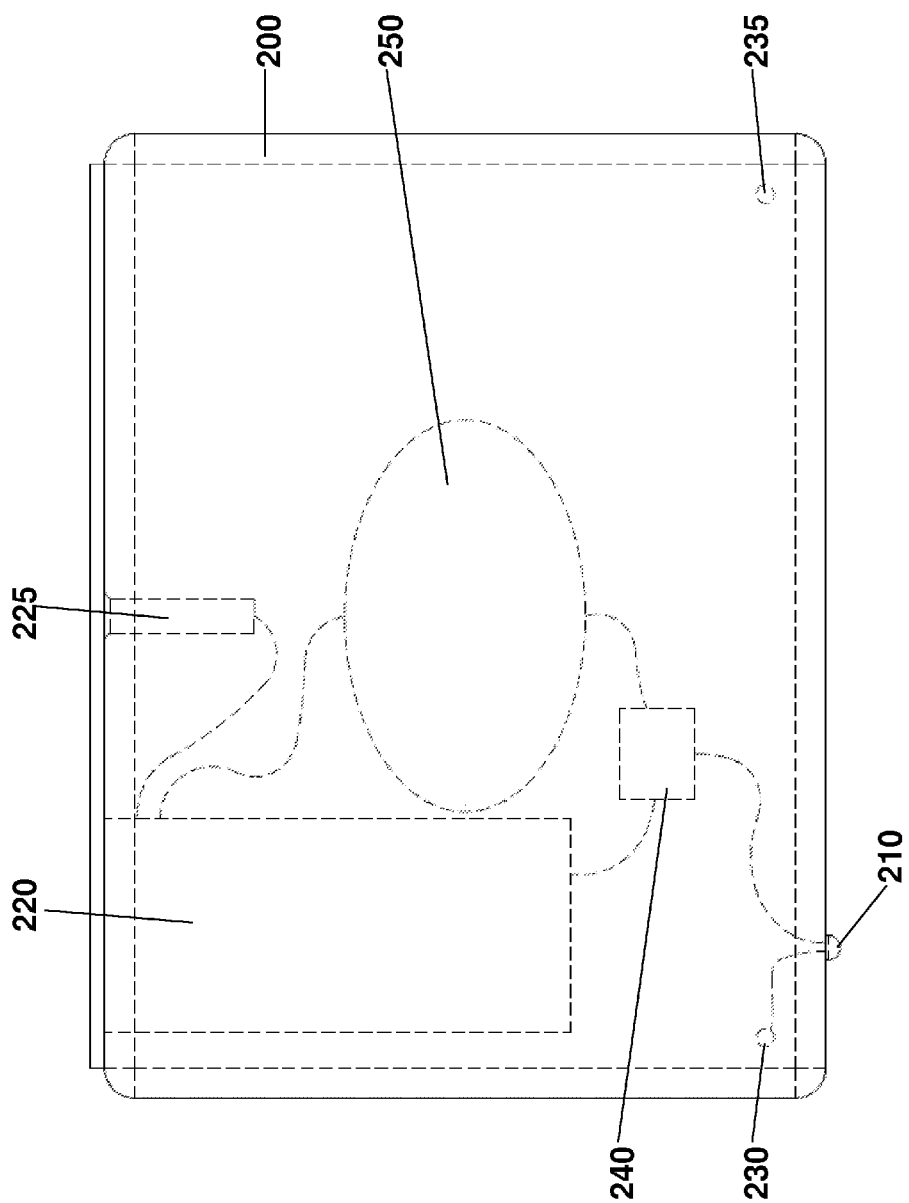
FIG. 7 is a transparent version of FIG. 3 showing, at a high level, devices within a bottom member in an embodiment of the disclosed technology.

FIG. 7 is a transparent version of FIG. 3 showing, at a high level, devices within a bottom member in an embodiment of the disclosed technology. The items shown within the bottom member 200 may instead or partially be within the top member 100. Electrical signals, such as by way of wires passing through the hinge 105 or pin/recess 130 and 230 or pin/recess 230 and 235 (shown and described with reference to FIG. 15) are used to detect whether the case is in an open or closed configuration, and allow or disallow the heating element to operate. Such an embodiment is desirable when some of the devices shown within the bottom member 200 of FIG. 7 are placed in the top member 100.

Referring again to FIG. 7, a semi-ovoid receptacle 250 (and corresponding semi-ovoid receptacle 150 of the top member 100) is cut into the bottom member 200 (and top member 100). "Ovoid," in embodiments of the disclosed technology refers to a solid generated from an oval curve in a plane, rotated around one of its axes of symmetry, an elongated sphere, or a three dimensional space resembling such a shape. The portable heater comprises a top member comprising a semi-ovoid cavity, a bottom member comprising a semi-ovoid cavity, a hinge operatively connected to the top and bottom members, and a heating mechanism. A heating plate, such as a metal heating plate, may form the receptacle or may be placed just behind a portion of the top/bottom member and is capable of generating heat based on passage of an electric charge there-through, such a charge emanating from a power source, such as one operatively connected to the power port 225, or a battery or batteries within the battery compartment 220. Light 210 alerts a user when a pad is ready to be placed in the ovoid receptacle, when a pad is being warmed, when a pad has reached a desired temperature, when it is safe to separate the top member 100 from the bottom member 200, and/or when to remove the pad.

Control circuitry 240 comprises the logic functions of the device, in an embodiment of the disclosed technology. In embodiments, functions may be carried out by switches such as temperature switches and timer switches which turn off the heat source or disconnect the power to the heating apparatus (e.g., the concave metal elements forming or just behind the ovoid receptacle) upon a certain amount of time having elapsed or a temperature having been reached. The control circuitry may also determine such events and determine when to turn on or off the heating apparatus or light 210. Other functions include detecting when the device is in an open or closed configuration, and disallowing heat in an open configuration, such as when pin 230 and recess 130 are not engaged. In such a case, a circuit may not be complete, thus disallowing power to the heating apparatus.

Figure 8:
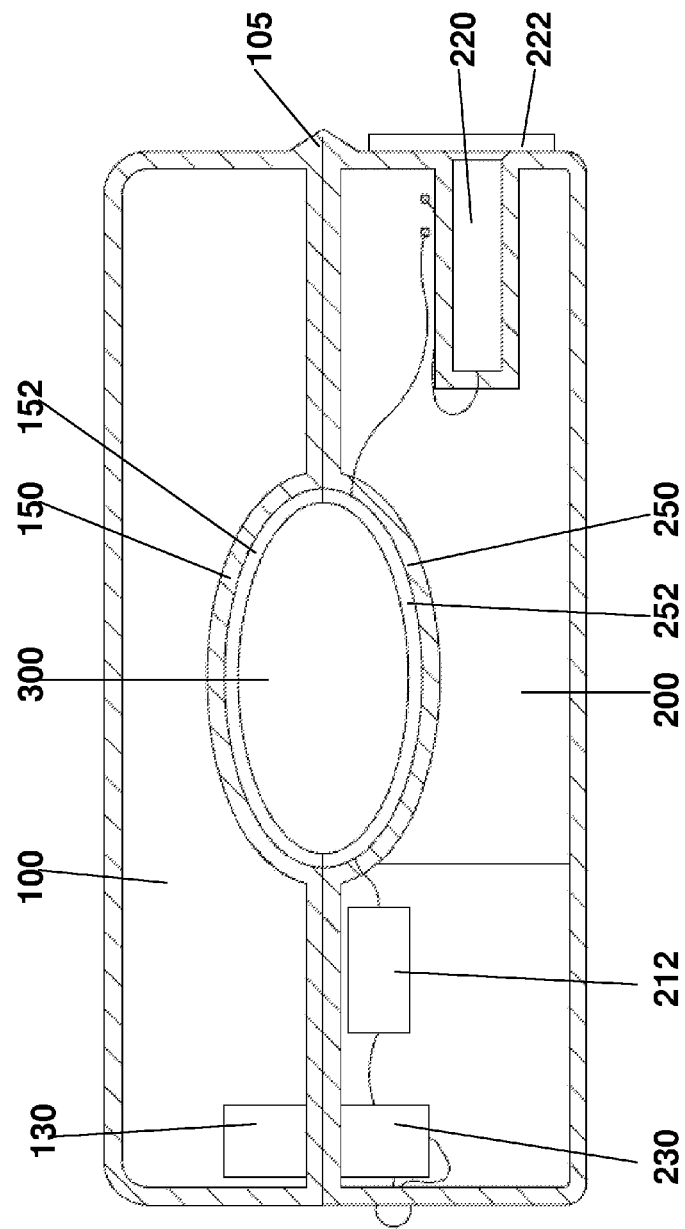
FIG. 8 shows a cutaway view of FIG. 3 along section line 8-8.

FIG. 8 shows a cutaway view of FIG. 3 along section line 8-8. In this figure, a pad 300 is shown and will be described in greater detail with reference to FIG. 9. The pad 300 is ovoid and placed within a cavity or recess formed between top member 100 and bottom member 200. A semi-ovoid receptacle 150 is formed within the top member 100, and a second semi-ovoid receptacle 250 is formed within the bottom member 200. A heating apparatus, such as a metal plate or other heat generating mechanism may form one or both semi-ovoid receptacles 150 or 250. Alternatively, such a heating apparatus may be placed just behind, or in front of, the receptacle itself, the receptacle wall and/or the top and bottom members 100 and 200 being procured from a hard plastic, polymer, metal, metal alloy, or combination thereof. As shown in FIG. 8, a heating mechanism comprises a first heatable plate 152 and a second heatable plate 252 which join when the device is in a closed configuration and the plates are operatively connected to a power source, i.e., when the battery compartment 220 (with cover 222) is operatively connected to a battery (power source) and a heating mechanism.

FIG. 9 shows a top perspective view of a pad adapted for placement in an ovoid cavity in an embodiment of the disclosed technology. FIG. 10 shows a top plan view of a pad adapted for placement in an ovoid cavity in an embodiment of the disclosed technology. FIG. 11 shows a side view of a pad adapted for placement in an ovoid cavity in an embodiment of the disclosed technology. The pad may be moistened with a detergent or a shampoo, such as what is commonly known as "baby shampoo." Baby shampoo is formulated so that it is less irritating to the eyes than regular shampoo and comprises one or a plurality of sodium trideceth sulfate, an organic surfactant, an ionic or non-ionic surfactant, an alcohol, or the like. Such a pad is typically pre-soaked and pre-packaged individually, so that a user may open a pad as necessary, and place it into the heating device. Such a pad may also be placed into the heating device while still in an individual package. Thus, when the pad has been heated to an appropriate temperature, the packaging is removed and it is ensured that the contents of the pad and detergent or shampoo do not remain on the heating device. Such pads, or such pads with packaging, in embodiments of the disclosed technology, are adapted to fit within and fill or substantially fill (e.g., 90% or greater by volume) an ovoid cavity formed when the heating device is in a closed configuration. Still further, the pad or its packaging may be foil-lined, as foil has a low heat capacity and aids in distribution of heat evenly over the pad. To aid in usability, the exterior of the pad may be porous and/or textured.

Figure 12:
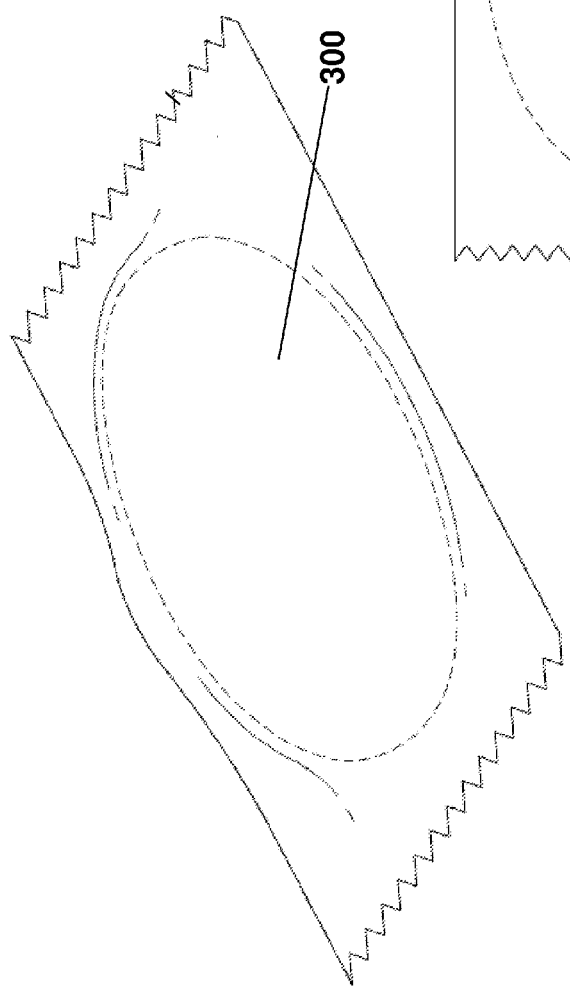
FIG. 12 shows a top perspective view of a packaged pad in an embodiment of the disclosed technology.
Figure 13:
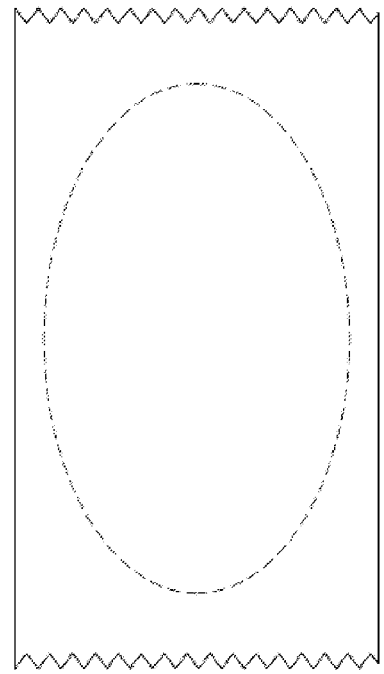
FIG. 13 shows a top plan view of a packaged pad in an embodiment of the disclosed technology.
Figure 14:
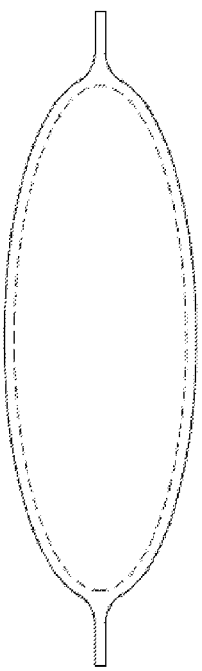
FIG. 14 shows a side view of a packaged pad in an embodiment of the disclosed technology.

FIG. 12 shows a top perspective view of a packaged pad in an embodiment of the disclosed technology. FIG. 13 shows a top plan view of a packaged pad in an embodiment of the disclosed technology. FIG. 14 shows a side view of a packaged pad in an embodiment of the disclosed technology. As described above, such a package, in embodiments of the disclosed technology, is placed within the heating device and more specifically, within the ovoid receptacle. The packaging, depending on the embodiment, may be removed before or after placement of the pad in the ovoid receptacle. A user may desire to remove part or all of the packaging before usage thereof to wipe away sebum on the face (e.g., near the eyes or under the eyelid) or other unwanted particles.

Figure 15:
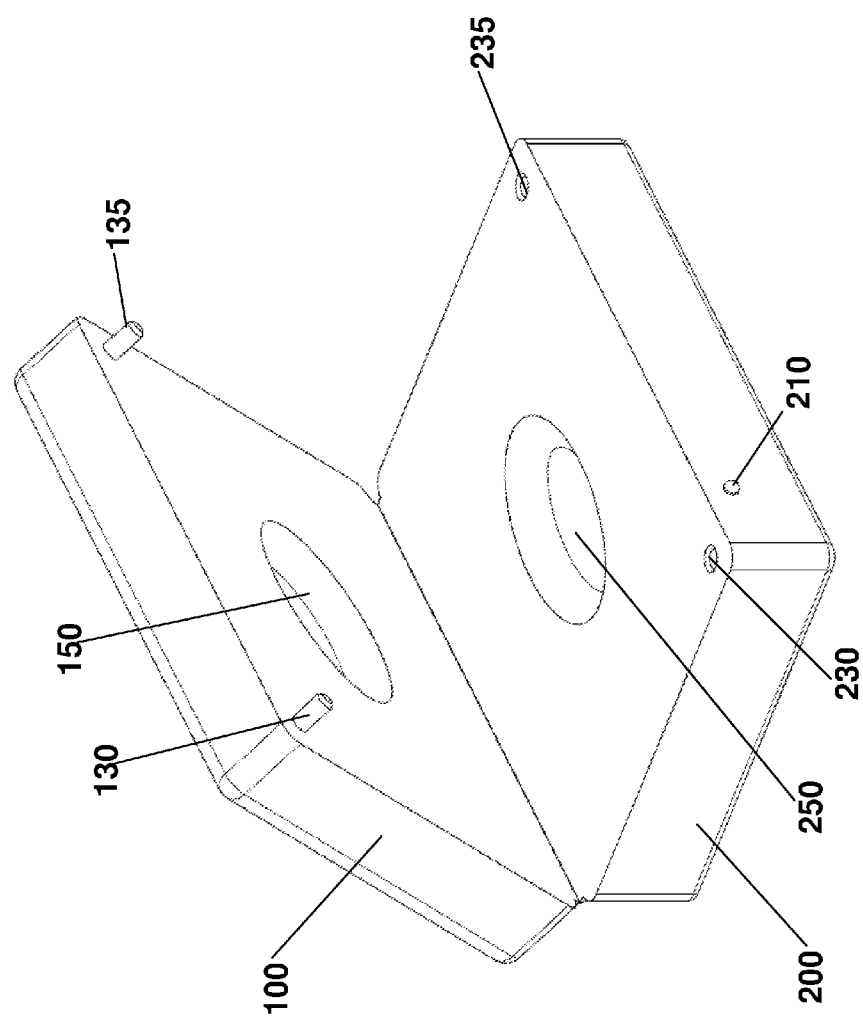
FIG. 15 shows a side perspective view of an eye-wiping device in an open configuration in an embodiment of the disclosed technology.
Figure 16:
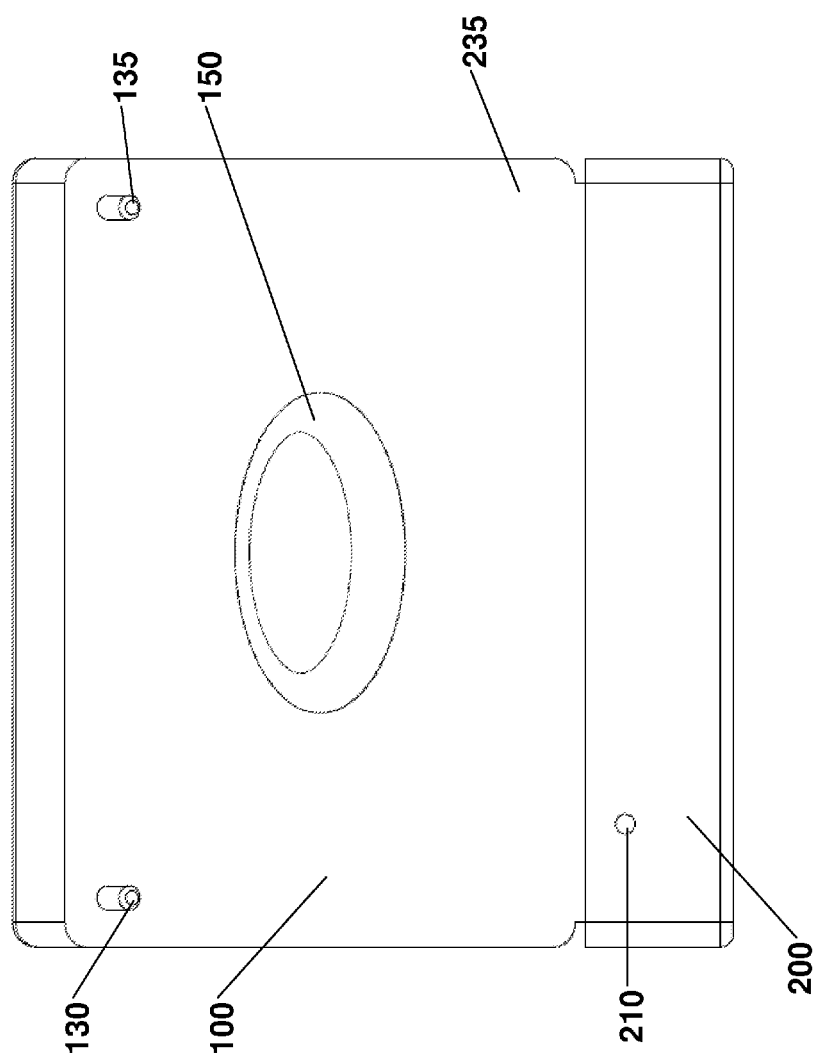
FIG. 16 shows a front side view of an eye-wiping device in an open configuration in an embodiment of the disclosed technology.

FIG. 15 shows a side perspective view of an eye-wiping device in an open configuration in an embodiment of the disclosed technology. FIG. 16 shows a front side view of an eye-wiping device in an open configuration in an embodiment of the disclosed technology. FIG. 17 shows a side view of an eye-wiping device in an open configuration in an embodiment of the disclosed technology. In the open configuration, pins 130 and 135 are clearly shown. The pins, as described above, interface with recesses 230 and 235. This ensures proper closure of the device, and, further, may be used in conjunction with an electrical or mechanical switch to determine whether the device is opened or closed. The heating apparatus, in embodiments of the disclosed technology, is only operative when the device is in a closed configuration.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

I claim:

1. A portable heater with ovoid receptacle comprising:
a top member comprising a semi-ovoid cavity;
a bottom member comprising a semi-ovoid cavity;
a hinge operatively connected to said top and bottom members;
an integrated electrical heating mechanism;
and a single detergent-soaked pad adapted for placement in a unitary ovoid cavity and sized to substantially fill said unitary ovoid cavity;
wherein said semi-ovoid cavities of said top and bottom members form said unitary ovoid cavity in a closed configuration of said portable heater.

2. The portable heater of claim 1, wherein said top member comprises at least one pin and said bottom member comprises at least one recess and said heating mechanism is operative only and is automatically activated when said at least one pin and said at least one recess interface.

3. The portable heater of claim 1, wherein each said semi-ovoid cavity is substantially identical to any other.

4. The portable heater of claim 1, wherein said pad is foil-lined.

5. The portable heater of claim 4, wherein said pad is textured.

6. The portable heater of claim 1 wherein said unitary ovoid cavity comprises a cavity enclosed in a solid generated from an oval curve in a plane, rotated around one of its axes of symmetry.

7. The portable heater of claim 1, wherein the electrical heating mechanism comprises:
   a battery compartment; and
   a first metal heating mechanism, the first metal heating mechanism being operatively connected to said battery compartment and to at least one of said semi-ovoid cavities.

8. The portable heater of claim 7, wherein the electrical heating mechanism further comprises a second metal heating mechanism, the second metal heating mechanism being operatively connected to said battery compartment and to at least one of said semi-ovoid cavities.

9. The portable heater of claim 1, wherein said pad is wrapped in foil.

10. A method for removing sebum from a face utilizing the portable heater of claim 1, comprising the steps of:
    warming said pad in said unitary ovoid cavity of said portable heater, said pad being textured;
    removing said pad from said heater;
    gently wiping said pad across at least a portion of said face.

11. The method of claim 10, wherein said textured pad is ovoid-shaped.

12. The method of claim 11, wherein said textured pad is pre-soaked in oil.

* * * * *